United States Patent [19]

Cooley

[11] Patent Number: 4,892,564
[45] Date of Patent: Jan. 9, 1990

[54] MEMBRANE PROCESS FOR HYDROCARBON LIQUID RECOVERY

[76] Inventor: Thomas E. Cooley, 5215 Spanish Oak, Houston, Tex. 77066

[21] Appl. No.: 172,670

[22] Filed: Mar. 24, 1988

[51] Int. Cl.⁴ ............................................. B01D 53/22
[52] U.S. Cl. ........................................ 55/16; 55/27; 55/68; 55/158; 55/268; 585/818
[58] Field of Search ...................... 55/16, 27, 68, 158, 55/267, 268; 585/818, 819

[56] References Cited

U.S. PATENT DOCUMENTS

| | | | |
|---|---|---|---|
| 2,497,421 | 2/1950 | Shiras | 55/27 X |
| 2,626,679 | 1/1953 | Harlow | 55/16 |
| 2,970,106 | 1/1961 | Binning et al. | 55/16 X |
| 2,985,588 | 5/1961 | Binning et al. | 585/819 |
| 3,324,626 | 6/1967 | Dresser et al. | 55/16 |
| 4,130,403 | 12/1978 | Cooley et al. | 55/16 |
| 4,367,135 | 1/1983 | Pasey, Jr. | 55/16 X |
| 4,374,657 | 2/1983 | Schendel et al. | 55/16 X |
| 4,547,205 | 10/1985 | Steacy | 55/27 X |
| 4,548,619 | 10/1985 | Steacy | 55/16 |
| 4,602,477 | 7/1986 | Lucadamo | 55/158 X |
| 4,654,063 | 3/1987 | Auvil et al. | 55/158 X |
| 4,659,343 | 4/1987 | Kelly | 55/16 |
| 4,717,407 | 1/1988 | Choe et al. | 55/158 X |
| 4,732,583 | 3/1988 | DeLong et al. | 55/16 |
| 4,738,691 | 4/1988 | Frey | 55/16 X |

FOREIGN PATENT DOCUMENTS 1107659 8/1981 Canada .

OTHER PUBLICATIONS

Grace Membrane Systems brochure, published Feb., 1988.

Primary Examiner—Robert Spitzer
Attorney, Agent, or Firm—Vincent L. Fabiano; William W. McDowell, Jr.

[57] ABSTRACT

Process and apparatus for separation of hydrogen, methane, and higher hydrocarbons from gas feed stock. For example, such feedstock is fed to a gas-liquid separator, the resulting gas is treated in a gas-gas membrane separator, the residue is separated in a second gas-liquid separator, and the permeate is separated in a second gas-gas membrane separator; the process may be repeated until the desired effluent specificity is achieved.

4 Claims, 1 Drawing Sheet

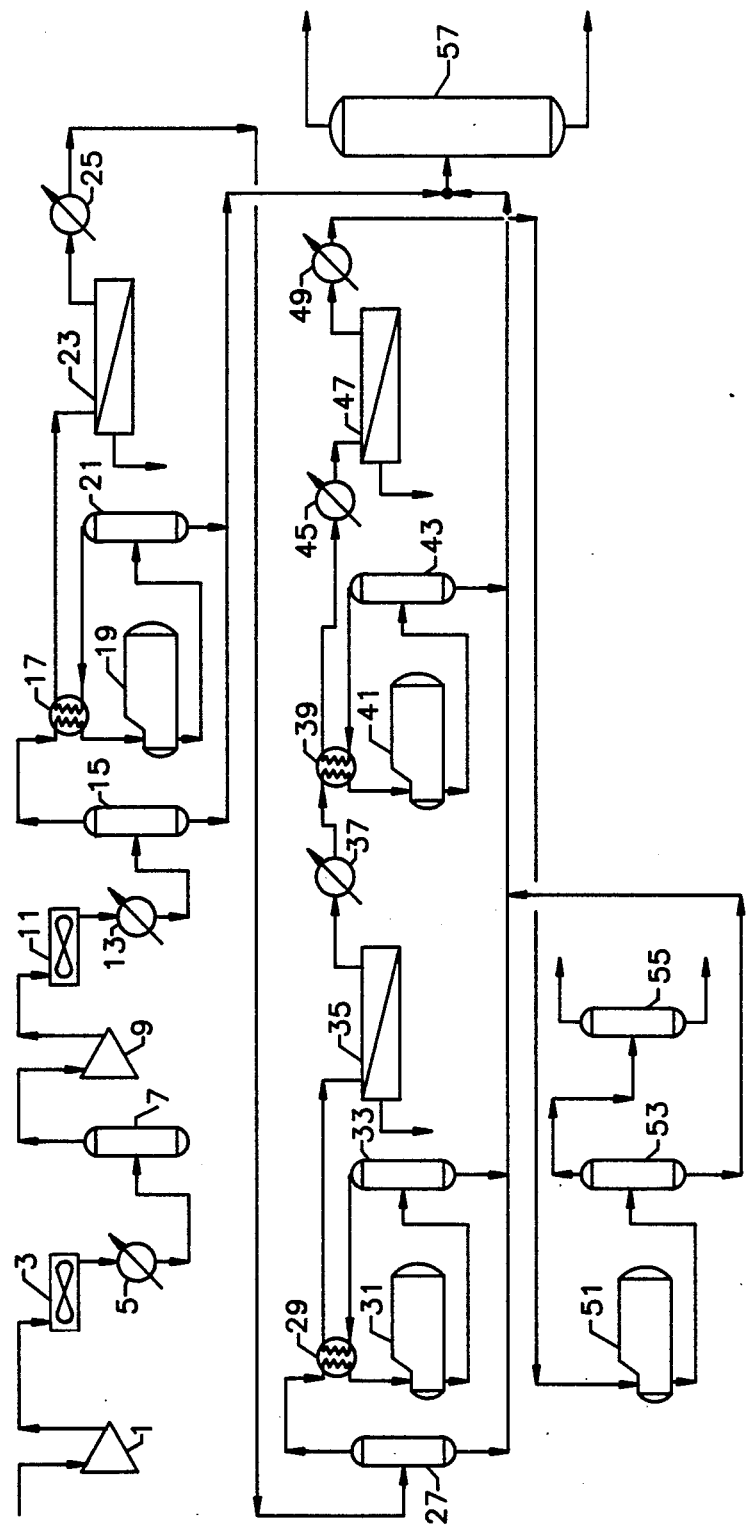

MEMBRANE PROCESS FOR HYDROCARBON LIQUID RECOVERY

FIELD OF THE INVENTION

The invention is directed to gas separation and is more particularly related to the separation of gases (principally hydrogen and methane) from liquids (principally C-3 and C-4 hydrocarbons) in feed stocks containing these compounds.

SUMMARY OF THE INVENTION

In brief, my invention effects gas separation by means of permeable membranes and gas-liquid separation in predetermined order and under carefully controlled conditions. The invention is of particular utility in gas-liquid separations of feedstocks where the liquids (C-3 and higher hydrocarbons) were formerly recovered by cryogenic processes. Save for a minor operation, the instant invention involves no cryogenic processes.

Computer Simulation

The process herein described and claimed has not been carried out in a plant. Rather, this is a computer-simulation based on conventional equipment, readily available from the suppliers of petrochemical apparatus. Certain preferences may be stated, particularly with regard to membrane modules. Given a specific feedstock and operational varables, the computer predicts with fair accuracy the composition of various streams within and exiting the process. A number of the more important of these streams are given in TABLES I and II. The crux of the invention is the selection of variables and the arrangement of streams.

The FIGURE is a schematic flow diagram of a preferred embodiment of the invention.

BACKGROUND OF THE INVENTION

My invention is specifically designed to replace a cryogenic unit normally employed in a process called Oleflex (Oleflex was developed by UOP). One of the process streams in the Oleflex process contains high levels of higher molecular weight hydrocarbon gases mixed with hydrogen and lower molecular weight hydrocarbons. A typical stream may have the following composition:

|  | Mole Percent |
|---|---|
| $H_2$ | 53.4 |
| Methane | 5.7 |
| Ethane | 1.3 |
| Ethylene | 0.2 |
| Propane | 14.6 |
| Propylene | 7.6 |
| Iso-Butane | 8.8 |
| Normal Butane | 0.3 |
| Butylene | 8.1 |
| $H_2S$ | 0.004 |

The purpose of the cryogenic unit in the Oleflex process is to condense and recover the propane and higher hydrocarbons as a liquid. These hydrocarbons have a higher value than the lighter hydrocarbon gases and are typically recovered for subsequent sale or use. Hydrogen and the lighter hydrocarbons can either be recycled to the Oleflex process or burned as fuel.

The membrane process of my invention offers several advantages over the cryogenic process. The first and perhaps most important advantage is that my membrane process eliminates the need for a cryogenic unit, thereby resulting in substantial capital and utility savings. Second, a variety of product streams is produced with my membrane process that can either be recombined to form two streams as in the cryogenic process or left as individual streams to be best utilized depending on the specific composition of that stream. Other advantages include:

(1) My membrane process can be carried out in carbon steel vessels. The cryogenic process requires stainless steel/aluminum.

(2) All cooling needs can be handled with cooling water.

(3) The membrane unit is smaller and lighter weight than the equivalent cryogenic unit.

(4) The complexity of a cryogenic unit is eliminated. Membranes and heat exchangers have no moving parts. This greatly reduces maintenance and downtime expenses.

(5) Membranes are flexible. Changes and additions to the systems are easily accommodated.

My entire process is accomplished without the need for a cryogenics unit. The lowest temperature required in my process is $-30°$ F., accomplished by a conventional refrigeration system to handle a gas stream that is only 8% of the volume of the original feed stream.

My system replaces a cryogenic unit that must be sizes for the full feed volume and be operated at $-200$ to $-250$-degrees F. The remainder of my membrane systems is operated at temperatures of $50°$ F. and above using standard heat exchangers and gas-liquid separation equipment in conjunction with the membranes. It is also an advantage of my invention that no additional compression is required and that the high methane fuel gas stream is delivered as close to the original feed gas pressure (allowing for some small pressure drops across each of the membrane units).

PRIOR ART

The use of membranes to separate gases is well known. A number of patent and literature references are given in my U.S. No. 4,130,403 (with A. B. Coady), of 1978. That patent in its entirety is herein incorporated by reference.

U.S. No. 4,659,343 to R. M. Kelly (1987) updates the literature and is herein incorporated in its entirety by reference. Both patents are directed to separation of carbon dioxide from gas streams. The instant invention does not involve carbon dioxide separation.

Canadian 1,107,659 (myself with A. B. Coady), 1981, discloses removal of water from hydrocarbons by dialysis through a cellulose ester membrane. The brochure, "Grace Membrane Systems", published by W. R. Grace & Co., describes membrane modules similar to those preferred for use in this instant invention.

DETAILED DESCRIPTION OF THE INVENTION

In the specific example that will be described below, a total of six streams (four in the gas phase, two in the liquid phase) is generated. The specific composition of these streams allows them to be used to best advantage in other applications, and this in turn provides enhanced economics over the two-stream cryogenic process. For example, there are three streams that have high levels of hydrogen (98.5%, 90.0%, and 84.8% $H_2$). These streams may be utilized as in various other processes or further purified with additional membranes to reach a specified purity. A fourth gas stream in my process contains a high level of methane (71%) that can be burned as fuel. My process generates two liquid streams. One contains hydrocarbons having an average molecular weight of 37.8 (high in methane, propane, and propylene). The other stream has an average molecular weight of 47.7 (high in propane, propylene, isobutane, and butylene). This last stream may be further stripped to provide two more streams if so desired, whereby ethane and lighters are removed.

What follows is a description combining the FIGURE and the TABLES. The reference to apparatus is to numbered elements in the FIGURE, whereas the reference to numbered streams is to streams in the TABLES.

The first several steps in the flow diagram of the FIGURE are concerned with taken the feedstock of Stream 1 (the so-called Oleflex feedstock) and bringing it to a pressure (about 350 psia) and temperature (about 300° F.) desirable in a feed stream (No. 4) for application in the process steps of my invention. To do this, Stream 1 enters compressor 1, where it is compressed (from 20.7 psia) to 90 psia. Compression increases the temperature (from 120° F. to 333.5° F.), and the stream must be cooled prior to further compression. For this it passes through fan 3, heat exchanger 5 (cooling water), surge tank 7, and emerges at 105° F. It is then compressed in compressor 9, from 90 to 350 psia. Compression again raises the temperature, here to 301.5° F., and again cooling is necessary prior to the first gas-liquid separator. Cooling is accomplished with fan cooler 11 and water cooler 13. The stream now enters gas-liquid separator 15, where it is separated into overhead gas (Stream 5) and liquid bottoms (Stream 6). Stream 6 has a high content of propylene, propane, iso-butane, and n-butane, and is joined with other liquid streams for further gas-liquid separation as hereinbefore described. The gas stream (Stream 7) from 15 is heat exchanged in heat exchanger 17 with a subsequent described stream, and passed through refrigerated chiller 19, where the stream temperature is reduced to 50° F. The latter stream enters gas-liquid separator 21, where it is separated into a gas stream (Stream 7) and a liquid stream (Stream 8), which joins Stream 6). Stream 7 passes through heat exchanger 17 and is heated from 50° F. to 120° F.) by Stream 5 above referenced. This stream leaves heat exchanger 17 as Stream 9, which is the feed to a first membrane separator 23. At this point note that this stream has a high hydrogen content (over 70 mole %), with minor amounts of methane and higher hydrocarbons.

The prior treatment as above described is designed specifically to produce a high hydrogen feed stream to membrane module, aiming at efficient separation and recovery of a first hydrogen stream. This is accomplished in membrane module 23, which provides a very high hydrogen permeate stream (Stream 11), for immediate recovery. Proceeding now with the non-permeate residue (Stream 10), this stream is cooled in water cooler 25 from 127.5° F. down to 100° F., and the stream now enters gas-liquid separator 27, where it separates as gas Stream 12 and liquid Stream 13. Liquid Stream 13 joins other liquid streams. Gas Stream 12 is treated identically to Stream 5,, i.e., it flows through a heat exchanger (29), a refrigerated chiller (31), a gas-liquid separator (33), the liquid Stream 15 joins other liquid streams, and the gas Stream 14 returns to heat exchanger 29, as feed Stream 16 to second membrane module 35. Membrane module 35 separates Stream 16 into a high hydrogen permeate (Stream 18), which can be recovered as such. The non-permeate residue, Stream 17, is cooled in cooler 37, then is treated in heat exchanger 34, refrigerated chiller 41, gas-liquid separator 43, and back to heat exchanger 39, in a manner very similar to the two preceding operations in units 17/19/21 and 29/31/33. Liquid effluent (Stream 21) from gas-liquid separator 43 joins with other liquid streams, and gas Stream 20 is warmed in heat exchanger 39 (from 50° F. to 120° F.), passed through cooling water heat exchanger 45, to provide feed for membrane module 47. The latter gives permeate Stream 24, high in hydrogen, which can be recovered as such, plus non-permeate Stream 23. The latter is cooled in water cooler 49, cooled again in refrigerated chiller 51, then sent to gas-liquid separator 53, where it yields gas Stream 25 and liquid Stream 27. The latter is sent with other liquid streams to final stripper 57. Gas Stream 26 goes to gas-liquid separator 55, where it yields gas Stream 29, useful as fuel, and liquid stream 30, with a major content of C-3 -hydrocarbons.

Liquid Stream 6, 8, 13, 15, 21, and 27 join to form the feed for stripper 57, where the final gas-liquid separation is made. The liquid effluent from Stripper 57 is mostly C-3 and higher hydrocarbons, and has an average molecular weight of 47.7.

Thus, may process gives three streams high in hydrogen (Streams 11, 18, and 24); a stream high in methane (Stream 29), a minor liquid stream high in C-3 hydrocarbons (Stream 30), and a major liquid stream high in C-3 and C-4 hydrocarbons (Stream 28).

TABLE I

| | Stream Summary | | | |
|---|---|---|---|---|
| | 1 | 2 | 3 | 4 |
| Stream | FEED | | | |
| Component | Mole fr | Mole fr | Mole fr | Mole fr |
| $H_2$ | .534348 | .534348 | .534348 | .534348 |
| $CH_4$ | .057462 | .057462 | .057462 | .057462 |
| $C_2H_4$ | .002305 | .002305 | .002305 | .002305 |
| $C_2H_6$ | .012903 | .012903 | .012903 | .012903 |
| $C_3H_6$ | .075899 | .075899 | .075899 | .075899 |
| $C_3H_8$ | .145707 | .145707 | .145707 | .145707 |
| $i-C_4H_{10}$ | .087777 | .087777 | .087777 | .087777 |
| $C_4H_8$ | .080842 | .080842 | .080842 | .080842 |
| $n-C_4H_{10}$ | .002717 | .002717 | .002717 | .002717 |
| $H_2S$ | .000041 | .000041 | .000041 | .000041 |
| Pressure psia | 20.700 | 90.000 | 90.000 | 350.000 |
| Flow lb mol/hr | 97841.270 | 9741.270 | 9741.270 | 9741.270 |
| Avg mole wt | 21.868 | 21.868 | 21.868 | 21.868 |
| Temp deg F. | 120.000 | 333.487 | 105.000 | 301.485 |
| | 5 | 6 | 7 | 8 |
| Stream | | | | |
| Component | Mole fr | Mole fr | Mole fr | Mole fr |
| $H_2$ | .545630 | .019936 | .704143 | .019970 |
| $CH_4$ | .058538 | .008407 | .072720 | .011505 |
| $C_2H_4$ | .002334 | .000987 | .002572 | .001543 |
| $C_2H_6$ | .013019 | .007624 | .013354 | .011906 |
| $C_2H_6$ | .075164 | .109411 | .053692 | .146367 |
| $C_3H_8$ | .143641 | .239899 | .095080 | .304680 |
| $i-C_4H_{.000025}$ | .336623E-05 | .295554 | .031914 | .253362 |
| $C_4H_8$ | .075897 | .306304 | .025742 | .242220 |
| $n-C_4H_{10}$ | .002517 | .011847 | .000743 | .008399 |
| $H_2S$ | .000041 | .000031 | .000040 | .000047 |
| Pres psia | 350.000 | 350.000 | 350.000 | 350.000 |
| Flow lb mole/hr | 9532.217 | 209.054 | 7323.736 | 2208.481 |
| Avg mole wt | 21.236 | 50.670 | 12.856 | 49.028 |
| Temp deg F. | 100.000 | 100.000 | 50.000 | 50.000 |
| | 9 | 10 | 11 | 12 |
| Stream | | | | |

TABLE I-continued

| Component | Mole fr | Mole fr | Mole fr | Mole fr |
|---|---|---|---|---|
| H₂ | .704143 | .350001 | .985202 | .356833 |
| CH₄ | .072720 | .154488 | .007827 | .157151 |
| C₂H₄ | .002572 | .005649 | .000130 | .005714 |
| C₂H₆ | .013354 | .029254 | .000735 | .029498 |
| C₃H₆ | .053692 | .119051 | .001822 | .118091 |
| C₃H₈ | .095080 | .000266 | .003504 | .207943 |
| i-C₄H₁₀ | .031914 | .071781 | .000274 | .068582 |
| C₄H₈ | .025742 | .057623 | .000440 | .054607 |
| n-C₄H₁₀ | .000743 | .001672 | .0020 .637442E-05 | .001567 |
| H₂S | .000040 | .000014 | .000060 | .000014 |
| Pressure psia | 350.000 | 350.000 | 55.000 | 350.000 |
| Flow lb mol/hr | 7323.736 | 3240.548 | 4083.187 | 3175.894 |
| Avg mole wt | 12.856 | 26.016 | 2.412 | 25.569 |
| Temp deg F. | 120.000 | 127.455 | 127.455 | 100.000 |

| Stream | 13 | 14 | 15 | 16 |
|---|---|---|---|---|
| Component | Mole fr | Mole fr | Mole fr | Mole fr |
| H₂ | .014386 | .502850 | .015449 | .502850 |
| CH₄ | .023691 | .209760 | .034153 | .209760 |
| C₂H₄ | .002441 | .006505 | .003863 | .006505 |
| C₂H₆ | .017243 | .030670 | .026759 | .030670 |
| C₃H₆ | .166178 | .080092 | .206931 | .080092 |
| C₃H₈ | .334475 | .129376 | .391630 | .129376 |
| i-C₄H₁₀ | .228916 | .023687 | .173546 | .023687 |
| C₄H₈ | .205805 | .016631 | .143392 | .016631 |
| n-C₄H₁₀ | .006855 | .000413 | .004262 | .000413 |
| H₂S | .000010 | .000014 | .000015 | .000014 |
| Pressure psia | 350.000 | 350.000 | 350.000 | 350.000 |
| Flow lb mole/hr | 64.654 | 2224.447 | 951.446 | 224.447 |
| Avg mole wt | 47.990 | 16.894 | 45.851 | 16.894 |
| Temp deg F. | 100.000 | 50.000 | 50.000 | 120.000 |

| Stream | 17 | 18 | 19 | 20 |
|---|---|---|---|---|
| Component | Mole fr | Mole fr | Mole fr | Mole fr |
| H₂ | .150001 | .900605 | .150000 | .208843 |
| CH₄ | .336216 | .067211 | .336216 | .443548 |
| C₂H₄ | .011351 | .001043 | .011351 | .012892 |
| C₂H₆ | .053150 | .005330 | .053150 | .055513 |
| C₃H₆ | .143345 | .008790 | .143345 | .101349 |
| C₃H₈ | .230512 | .015369 | .230512 | .150543 |
| i-C₄H₁₀ | .044100 | .000677 | .044100 | .016742 |
| C₄H₈ | .030553 | .000938 | .030553 | .010339 |
| n-C₄H₁₀ | .000770 | .000012 | .000770 | .000228 |
| H₂S | .336623E-05 | .000025 .336623E-05 .329183E-05 | | |
| Pressure psia | 350.000 | 65.000 | 350.000 | 350.000 |
| Flow lb mole/hr | 1178.762 | 1045.685 | 1178.762 | 834.750 |
| Avg mole wt | 28.132 | 4.225 | 28.132 | 22.038 |
| Temp deg F. | 127.405 | 127.405 | 100.000 | 50.000 |

| Stream | 21 | 22 | 23 | 24 |
|---|---|---|---|---|
| Component | Mole fr | Mole fr | Mole fr | Mole fr |
| H₂ | .007219 | .208843 | .100000 | .848126 |
| CH₄ | .075773 | .443548 | .498731 | .119430 |
| C₂H₄ | .007612 | .012892 | .014811 | .001624 |
| C₂H₆ | .047415 | .055513 | .063667 | .007622 |
| C₃H₆ | .245250 | .101349 | .117146 | .008564 |
| C₃H₈ | .424556 | .150543 | .173822 | .013819 |
| i-C₄H₁₀ | .110484 | .016742 | .019532 | .000357 |
| C₄H₈ | .079602 | .010339 | .012025 | .000439 |
| n-C₄H₁₀ | .002084 | .000228 | .000266 .485718E-05 | |
| H₂S | .354679E-05 | .329183E-05 | .132724E-05 | .000015 |
| Pressure psia | 350.000 | 350.000 | 350.000 | 15.000 |
| Flow lb mol/hr | 344.012 | 834.750 | 713.305 | 121.445 |
| Avg mole wt | 42.921 | 22.038 | 24.953 | 4.917 |
| Temp deg F. | 50.000 | 120.000 | 122.419 | 122.419 |

| Stream | 25 | 26 | 27 | 28 |
|---|---|---|---|---|
| Component | Mole fr | Mole fr | Mole fr | Mole fr |
| H₂ | .100000 | .106713 | .003871 | .017406 |
| CH₄ | .498731 | .527131 | .092067 | .023938 |
| C₂H₄ | .014811 | .015217 | .008995 | .002742 |
| C₂H₆ | .063667 | .064296 | .054652 | .019172 |
| C₃H₆ | .117146 | .107545 | .254643 | .169963 |
| C₃H₈ | .173822 | .155968 | .429496 | .335578 |
| i-C₄H₁₀ | .019532 | .014469 | .092032 | .220580 |
| C₄H₈ | .012025 | .008483 | .062747 | .203706 |
| n-C₄H₁₀ | .000266 | .000176 | .001546 | .006881 |
| H₂S | .132724E-05 | .132172E-05 | .140623E-05 | .000033 |
| Pressure psia | 350.000 | 350.000 | 350.000 | 350.000 |
| Flow lb mol/hr | 713.305 | 666.746 | 46.559 | 3824.206 |
| Avg mole wt | 24.953 | 23.763 | 41.995 | 47.674 |
| Temp deg F. | 100.000 | 50.000 | 50.000 | 53.928 |

| Stream | 29 | 30 |
|---|---|---|
| Component | Mole fr | Mole fr |
| H₂ | .159268 | .004070 |
| CH₄ | .710375 | .169245 |
| C₂H₄ | .013882 | .017824 |
| C₂H₆ | .046860 | .098351 |
| C₃H₆ | .030278 | .258451 |
| C₃H₈ | .037440 | .387462 |
| i-C₄H₁₀ | .001283 | .040222 |
| C₄H₈ | .000603 | .023872 |
| n-C₄H₁₀ | .000010 | .000501 |
| H₂S | .806794E-06 | .232741E-05 |
| Pressure psia | 350.000 | 350.000 |
| Flow lb mol/hr | 440.965 | 225.782 |
| Avg mole wt | 16.550 | 37.849 |
| Temp deg F. | −30.000 | −30.000 |

Performance of the three membranes, 23, 35, and 47, is given below.

Membrane 23

| | |
|---|---|
| Total area | 121,540.808 ft² |
| Permeate pressure | 55.000 psia |
| Pressure drop | 10.000 psia |

| Component | Pct recovery | Permeate mole-frac | Permeation rate (scf/ft 2/hr/100 psi) |
|---|---|---|---|
| H₂ | 78.01 | .98520 | 9.960 |
| CH₄ | 6.00 | .78266E-02 | .262 |
| C₂H₄ | 2.82 | .12998E-02 | .120 |
| C₂H₆ | 3.07 | .73534E-03 | .131 |
| C₃H₆ | 1.89 | .18220E-02 | .080 |
| C₃H₈ | 2.05 | .35043E-02 | .087 |
| i-C₄H₁₀ | .48 | .27366E-03 | .020 |
| C₄H₈ | .95 | .43989E-03 | .040 |
| n-C₄H₁₀ | .48 | .63744E-05 | .020 |
| H₂S | 84.14 | .59691E-04 | 13.750 |

Membrane 31

| | |
|---|---|
| Total area | 106,893.241 ft² |
| Permeate pressure | 65.000 psia |
| Pressure drop | 10.000 psia |

| Component | Pct recovery | Permeate mole-frac | Permeation rate (scf/ft 2/hr/100 psi) |
|---|---|---|---|
| H₂ | 84.19 | .90061 | 9.960 |
| CH₄ | 15.06 | .67211E-01 | .262 |
| C₂H₄ | 7.54 | .10430E-02 | .120 |
| C₂H₆ | 8.17 | .53299E-02 | .131 |
| C₃H₆ | 5.16 | .87900E-02 | .080 |
| C₃H₈ | 5.58 | .15369E-01 | .087 |
| i-C₄H₁₀ | 1.34 | .67713E-03 | .020 |
| C₄H₈ | 2.65 | .93775E-03 | .040 |
| n-C₄H₁₀ | 1.34 | .11818E-04 | .020 |
| H₂S | 87.01 | .25425E-04 | 13.750 |

Membrane 47

| | |
|---|---|
| Total area | - 12,871.551 ft² |
| Permeate pressure | 15 psia |
| Pressure drop | - 10.000 psia |

| Component | Pct recovery | Permeate mole-frac | Permeation rate (scf/ft 2/hr/100 psi) |
|---|---|---|---|
| H₂ | 59.08 | .84813 | 9.960 |
| CH₄ | 3.92 | .11943 | .262 |

TABLE I-continued

| | | | |
|---|---|---|---|
| $C_2H_4$ | 1.83 | .16241E-02 | .120 |
| $C_2H_6$ | 2.00 | .76218E-02 | .131 |
| $C_3H_6$ | 1.23 | .85636E-02 | .080 |
| $C_3H_8$ | 1.34 | .13819E-01 | .087 |
| $i$-$C_4H_{10}$ | .31 | .35692E-03 | .020 |
| $C_4H_8$ | .62 | .43949E-03 | .040 |
| $n$-$C_4H_{10}$ | .31 | .48572E-05 | .020 |
| $H_2S$ | 65.55 | .14831E-04 | 13.750 |

In my preferred embodiment a cellulose ester membrane which is a blend of cellulose acetates and which is spirally wound in a module is used. The membrane and module are produced by Grace Membrane Systems, Houston, TX. These membranes exhibit a permeability constant for carbon dioxide and hydrogen of at least 4 scf/ft$^2$/hr/100 psi (6.2×10$^{-5}$ cm$^3$/cm$^2$/sec/cm Hg).

These spiral wrap modules consist of a cylinder within a cylinder arrangement wherein the membrane is wound around the inner cylinder before being placed in the outer cylinder or casing. The inner cylinder is made from a polymeric material which has a series of longitudinal perforations to which one end of the membrane is affixed. The remainder of the membrane is wrapped around the inner supporting cylinder, and this inner cylinder wrapped with the membrane is disposed within the larger casing cylinder. The casing cylinder is enclosed on both ends by enclosing heads.

On one end, there are two orifices. Through one orifice the feed gas is introduced and, as the feed gas passes over the membrane, the more permeable components of the gaseous mixture pass through the membrane and into and through the longitudinal perforations of the inner cylinder at a higher rate than the other components of the mixture. This permeate gas then flows through the inner cylinder in a direction countercurrent to that of the feed gas. The permeate gas is withdrawn through the same enclosing head as the feed; however, the permeate stream is withdrawn through the orifice connecting the inner cylinder with the encasing head orifice. That portion of the feed stream which does not permeate through and into the inner cylinder passes over the membrane and out the opposite side of the module through an orifice in the other encasing head.

As an alternate to the above-described modules, membrane systems that are in the form of hollow fibers may also be employed in the present invention. Numerous geometrical variations are possible using either module system.

Broadly speaking, my invention is directed to a method of separating components of a feedstock into one or more gas streams comprising mostly hydrogen or methane, and one or more liquid streams comprising mostly C-3 (propylene and propane) and higher hydrocarbons, said method comprising:
(a) subjecting the said feedstock to one or more gas-liquid separations wherein the gas effluent is the feed to the next separation;
(b) subjecting the gas effluent from (a) to one or more gas-gas membrane separations wherein the gas residue from the membrane is a feed to a succeeding gas-liquid separation;
(c) combining a major amount of liquid effluents from the above (a) and (b); and
(d) subjecting the said combined effluents to a stripping operation to provide a final liquid product.

In a narrower sense my invention comprises (1) subjecting the above described feedstock to gas-liquid separation at about 350 psia and about 100° F. to provide a gas stream and a liquid stream;
(2) subjecting the gas stream from (1) to a gas-liquid separation at about 350 psia and about 50° F. to provide an exit gas stream and a liquid stream;
(3) subjecting the exit gas stream from (2) to first gas-gas membrane separation to provide a high hydrogen permeate gas and a residue gas;
(4) subjecting the residue gas from (3) to a gas-liquid separation to provide an exit gas stream and a liquid stream;
(5) subjecting the exit gas stream from (4) to a gas-liquid separation to provide a gas effluent and a liquid stream;
(6) subjecting the gas effluent from (5) to a second gas-gas membrane separation to provide a high hydrogen permeate gas and a residue gas;
(7) subjecting the residue gas from (6) to a gas-liquid separation to provide a gas effluent and a liquid effluent;
(8) subjecting the gas effluent from (7) to a third gas-gas membrane separation to provide a high hydrogen permeate gas and a residue gas;
(9) subjecting the residue gas of (8) to a gas-liquid separation to provide an exit gas stream and a liquid stream;
(10) subjecting the exit gas stream from (9) to a gas-liquid separation to provide a gas stream high in methane and a liquid stream of average molecular weight about 37.8;
(11) combining liquid effluent streams made in (1), (2), (4), (5), (7), (9), and (10); and
(12) subjecting the combined streams of (11) to a gas-liquid separation, thereby to provide a fuel gas stream and a liquid effluent having an average molecular weight of about 47 and comprising C-3 and higher hydrocarbons.

In a very specific embodiment the invention starts with a feedstock consisting essentially of Stream 4 below;
(1) that feestock is subjected to a first gas-liquid separation to provide a stream consisting essentially of gas Stream 5 below and a liquid stream consisting essentially of Stream 6 below;
(2) Stream 5 from (1) is subjected to a second gas-liquid separation to provide an exit gas stream consisting essentially of Stream 7 below and a liquid stream consisting essentially of Stream 8 below;
(3) Stream 7 from (2) is subjected to a first gas-gas membrane separation to provide a permeate gas stream consisting essentially of Stream 11 below and a residue gas stream consisting essentially of Stream 10 below;
(4) Stream 10 from (3) is subjected to a third gas-liquid separation to provide an exit gas stream consisting essentially of Stream 12 below and a liquid stream consisting essentially of Stream 13 below;
(5) Stream 12 from (4) is subjected to a fourth gas-liquid separation to provide a gas effluent consisting essentially of Stream 14 below and a liquid effluent consisting essentially of Stream 15 below;
(6) Stream 14 from (5) is subjected to a second gas-gas membrane separation to provide a high hydrogen permate gas consisting essentially of Stream 18 below and a residue gas consisting essentially of Stream 17 below;

(7) Stream 17 from (6) is subjected to a fifth gas-liquid separation to provide a gas effluent consisting essentially of Stream 20 below and a liquid effluent consisting essentially of Stream 21 below;

(8) Stream 20 from (7) is subjected to a third gas-gas membrane separation to provide a permeate gas consisting esssentially of Stream 24 below and a residue gas consisting essentially of Stream 23 below;

(9) Stream 23 from (8) is subjected to a sixth gas-liquid separation to provide an exit gas stream consisting essentially of Stream 26 below and a liquid stream consisting essentially of Stream 25 below;

(10) Stream 26 and from (9) is subjected to a seventh gas-liquid separation to provide a gas stream consisting essentially of Stream 29 below and a liquid stream consisting essentially of Stream 30 below;

(11) Combining liquid effluent Streams 6, 8, 13, 15, 21, 25, and 30;

(12) subjecting the combined streams of (11) to an eighth gas-liquid separation to provide a fuel gas stream and a liquid effluent consisting essentially of Stream 28.

The above identified numbered streams are the same as those in the TABLE, rounded off to three significant figures, viz.:

| Stream No. | $H_2$ Mole Fraction | $CH_4$ Mole Fraction | $C_2H_4$ Mole Fraction | $C_2H_6$ Mole Fraction | $C_3H_6$ Mole Fraction | $C_3H_8$ Mole Fraction | $i\text{-}C_4H_{10}$ Mole Fraction | $C_4H_8$ Mole Fraction | $n\text{-}C_4H_{10}$ Mole Fraction | $H_2S$ Mole Fraction |
|---|---|---|---|---|---|---|---|---|---|---|
| 5  | .546 | .059 | .002 | .013 | .075 | .144 | .083 | .076 | .003 | .000 |
| 6  | .020 | .008 | .001 | .008 | .109 | .240 | .296 | .306 | .012 | .000 |
| 7  | .704 | .073 | .003 | .013 | .054 | .095 | .032 | .026 | .001 | .000 |
| 8  | .020 | .012 | .002 | .012 | .146 | .305 | .253 | .242 | .008 | .000 |
| 10 | .350 | .154 | .006 | .029 | .119 | .210 | .072 | .058 | .002 | .000 |
| 11 | .985 | .008 | .000 | .001 | .002 | .004 | .000 | .000 | .000 | .000 |
| 12 | .357 | .157 | .006 | .029 | .118 | .208 | .069 | .055 | .002 | .000 |
| 13 | .014 | .024 | .002 | .017 | .166 | .334 | .229 | .206 | .007 | .000 |
| 14 | .503 | .209 | .007 | .031 | .080 | .129 | .024 | .017 | .000 | .000 |
| 15 | .015 | .034 | .004 | .027 | .207 | .392 | .174 | .143 | .004 | .000 |
| 17 | .150 | .336 | .011 | .053 | .143 | .231 | .044 | .031 | .001 | .000 |
| 18 | .900 | .067 | .001 | .005 | .009 | .015 | .001 | .001 | .000 | .000 |
| 20 | .209 | .443 | .013 | .056 | .101 | .151 | .017 | .010 | .000 | .000 |
| 21 | .007 | .076 | .008 | .047 | .245 | .424 | .110 | .080 | .002 | .000 |
| 23 | .100 | .499 | .015 | .064 | .117 | .174 | .020 | .012 | .000 | .000 |
| 24 | .848 | .119 | .002 | .008 | .009 | .014 | .000 | .000 | .000 | .000 |
| 25 | .100 | .499 | .015 | .064 | .117 | .174 | .020 | .012 | .000 | .000 |
| 26 | .107 | .527 | .015 | .064 | .108 | .156 | .014 | .008 | .000 | .000 |
| 28 | .017 | .024 | .003 | .019 | .170 | .336 | .221 | .204 | .007 | .000 |
| 29 | .159 | .710 | .014 | .047 | .030 | .037 | .001 | .001 | .000 | .000 |
| 30 | .004 | .169 | .018 | .098 | .258 | .387 | .040 | .024 | .001 | .000 |

The invention also contemplates a novel arrangement of apparatus to accomplish the separations described, to wit: in combination a gas-liquid separator with conduit for leading gas effluent to a second gas-liquid separator, which latter has a conduit for leading gas effluent to a first gas-gas membrane separator, said first membrane separator having exit conduits for permeate and residue gases the latter residue gas conduit leading to a third gas-liquid separator with gas and liquid exit conduits; said gas exit conduit leading to a fourth gas-liquid separator with gas and liquid exit conduits; said gas exit conduit leading to a second gas-gas membrane separator with exit conduits for permeate and residue gases; said residue gas conduit leading to a fifth gas-liquid separator, with gas and liquid conduits; said gas exit conduit leading to a third gas-gas membrane separator having exit conduits for permeate and residue gases; said gas conduit leading to a sixth gas-liquid separator with gas and liquid exit conduits, said gas exit conduit leading to a seventh gas-liquid separator with gas and liquid exit conduits; the liquid exit conduits in the first, second, third, fourth, fifth, and sixth gas-liquid separators being joined into a conduit feeding to a seventh gas-liquid separator or stripper with gas and liquid exit ports.

I claim:

1. Method of separating components of a feedstock into one or more gas streams comprising mostly hydrogen or methane, and one or more liquid streams comprising mostly C-3 and higher hydrocarbons, comprising:
   (a) subjecting the said feedstock to one or more gas-liquid separations producing a gas effluent and a liquid effluent wherein the gas effluent is a feed to a next separation;
   (b) subjecting the gas effluent from (a) to one or more gas-gas membrane separations producing a gas residue from the membrane wherein the gas residue from the membrane is cooled producing a gas and liquid mixture and is a feed to a succeeding gas-liquid separation producing a gas effluent and a liquid effluent;
   (c) combining a major amount of liquid effluents from the above (a) and (b); and
   (d) subjecting the effluents combined in Step (c) to a stripping operation to provide a final liquid product.

2. Method according to claim 1 wherein
Step (a) comprises:
   (1) subjecting said feedstock to gas-liquid separation at about 350 psia and about 100° F. to provide a gas stream and a liquid stream; and
   (2) subjecting the gas stream from (1) to a gas-liquid separation at about 350 psia and about 50° F. to provide an exit gas stream and a liquid stream;
Step (b) comprises:
   (3) subjecting the exit gas stream from (2) to first gas-gas membrane separation to provide a high hydrogen permeate gas and a residue gas;
   (4) subjecting the residue gas from (3) to a gas-liquid separation to provide an exit gas stream and a liquid stream;
   (5) subjecting the exit gas stream from (4) to a gas-liquid separation to provide a gas effluent and a liquid stream;

(6) subjecting the gas effluent from (5) to a second gas-gas membrane separation to provide a high hydrogen permeate gas and a residue gas;
(7) subjecting the residue gas from (6) to a gas-liquid separation to provide a gas effluent and a liquid effluent;
(8) subjecting the gas effluent from (7) to a third gas-gas-membrane separation to provide a high hydrogen permeate gas and a residue gas;
(9) subjecting the residue gas of (8) to a gas-liquid separation to provide an exit gas stream and a liquid stream; and
(10) subjecting the exit gas stream from (9) to a gas-liquid separation to provide a gas stream high in methane and a liquid stream of average molecular weight about 37.8;

Step (c) comprises:
(11) combining liquid effluent streams made in (1), (2), (4), (5), (7), (9), and (10); and Step (d) comprises:
(12) subjecting the combined streams of (11) to a gas-liquid separation, thereby to provide a fuel gas stream and a liquid effluent having an average molecular weight of about 47 and comprising C-3 and higher hydrocarbons.

3. Method according to claim 2 wherein the streams correspond to those in the table below and wherein Step (a) further comprises:
(1) subjecting a feedstock consisting essentially of Stream 4 to a first gas-liquid separation to provide a stream consisting essentially of gas Stream 5 and a liquid stream consisting essentially of Stream 6; and
(2) subjecting Stream 5 from (1) to a second gas-liquid separation to provide an exit gas stream consisting essentially of Stream 7 and a liquid stream consisting essentially of Stream 8;

Step (b) further comprises:
(3) subjecting Stream 7 from (2) to a first gas-gas membrane separation to provide a permeate gas stream consisting essentially of Stream 11 and a residue gas stream consisting essentially of Stream 10;
(4) subjecting Stream 10 from (3) to a third gas-liquid separation to provide an exit gas stream consisting essentially of Stream 12 and a liquid stream consisting essentially of Stream 13;
(5) subjecting Stream 12 from (4) to a fourth gas-liquid separation to provide a gas effluent consisting essentially of Stream 14 and a liquid effluent consisting essentially of Stream 15;
(6) subjecting Stream 14 from (5) to a second gas-gas membrane separation to provide a high hydrogen permeate gas consisting essentially of Stream 18 and a residue gas consisting essentially of Stream 17;
(7) subjecting Stream 17 from (6) to a fifth gas-liquid separation to provide a gas effluent consisting essentially of Stream 20 and a liquid effluent consisting essentially of Stream 21;
(8) subjecting Stream 20 from (7) to a third gas-gas membrane separation to provide a permeate gas consisting essentially of Stream 24 and a residue gas consisting essentially of Stream 23;
(9) subjecting Stream 23 from (8) to a sixth gas-liquid separation to provide an exit gas stream consisting essentially of Stream 26 and a liquid stream consisting essentially of Stream 25; and
(10) subjecting Stream 26 from (9) to a seventh gas-liquid separation to provide a gas stream consisting essentially of Stream 29 and a liquid stream consisting essentially of Stream 30;

Step (c) further comprises:
(11) Combining liquid effluent Streams 6, 8, 13, 15, 21, 25, and 30; and Step (d) further comprises:
(12) subjecting the combined streams of (11) to an eighth gas-liquid separation to provide a fuel gas stream and a liquid effluent consisting essentially of Stream 28;

The above identified numbered streams being:

| Stream No. | $H_2$ Mole Fraction | $CH_4$ Mole Fraction | $C_2H_4$ Mole Fraction | $C_2H_6$ Mole Fraction | $C_3H_6$ Mole Fraction | $C_3H_8$ Mole Fraction | $i\text{-}C_4H_{10}$ Mole Fraction | $C_4H_8$ Mole Fraction | $n\text{-}C_4H_{10}$ Mole Fraction | $H_2S$ Mole Fraction |
|---|---|---|---|---|---|---|---|---|---|---|
| 4 | .534 | .057 | .002 | .013 | .076 | .146 | .088 | .081 | .003 | .000 |
| 5 | .546 | .059 | .002 | .013 | .075 | .144 | .083 | .076 | .003 | .000 |
| 6 | .020 | .008 | .001 | .008 | .109 | .240 | .296 | .306 | .012 | .000 |
| 7 | .704 | .073 | .003 | .013 | .054 | .095 | .032 | .026 | .001 | .000 |
| 8 | .020 | .012 | .002 | .012 | .146 | .305 | .253 | .242 | .008 | .000 |
| 10 | .350 | .154 | .006 | .029 | .119 | .210 | .072 | .058 | .002 | .000 |
| 11 | .985 | .008 | .000 | .001 | .002 | .004 | .000 | .000 | .000 | .000 |
| 12 | .357 | .157 | .006 | .029 | .118 | .208 | .069 | .055 | .002 | .000 |
| 13 | .014 | .024 | .002 | .017 | .166 | .334 | .229 | .206 | .007 | .000 |
| 14 | .503 | .209 | .007 | .031 | .080 | .129 | .024 | .017 | .000 | .000 |
| 15 | .015 | .034 | .004 | .027 | .207 | .392 | .174 | .143 | .004 | .000 |
| 17 | .150 | .336 | .011 | .053 | .143 | .231 | .044 | .031 | .001 | .000 |
| 18 | .900 | .067 | .001 | .005 | .009 | .015 | .001 | .001 | .000 | .000 |
| 20 | .209 | .443 | .013 | .056 | .101 | .151 | .017 | .010 | .000 | .000 |
| 21 | .007 | .076 | .008 | .047 | .245 | .424 | .110 | .080 | .002 | .000 |
| 23 | .100 | .499 | .015 | .064 | .117 | .174 | .020 | .012 | .000 | .000 |
| 24 | .848 | .119 | .002 | .008 | .009 | .014 | .000 | .000 | .000 | .000 |
| 25 | .100 | .499 | .015 | .064 | .117 | .174 | .020 | .012 | .000 | .000 |
| 26 | .107 | .527 | .015 | .064 | .108 | .156 | .014 | .008 | .000 | .000 |
| 28 | .017 | .024 | .003 | .019 | .170 | .336 | .221 | .204 | .007 | .000 |
| 29 | .159 | .710 | .014 | .047 | .030 | .037 | .001 | .001 | .000 | .000 |
| 30 | .004 | .169 | .018 | .098 | .258 | .387 | .040 | .024 | .001 | .000 |

4. Apparatus including gas-liquid separators including gas exit conduits and liquid exit conduits comprising in combination a first gas-liquid separator with conduit (1) for leading gas effluent to a second gas-liquid separator, which latter has a conduit (2) for leading gas effluent to a first gas-gas membrane separator, said first membrane separator having a permeate gas exit conduit (3) and a residue gas exit conduit (4); the residue gas conduit (4) leading to a third gas-liquid separator with a gas exit conduit (5) and a liquid exit conduit (6); the gas exit conduit (5) leading to a fourth gas-liquid separator with a gas exit conduit (7) and a liquid exit conduit (8); said gas exit conduit (7) leading to a second gas-gas membrane separator with a permeate exit conduit (9) and a residue gas exit conduit (10); said residue exit conduit (10) leading to a fifth gas-liquid separator, with a gas exit conduit (11) and a liquid exit conduit (12); the gas exit conduit (11) leading to a third gas-gas membrane separator having a permeate gas exit conduit (13) and a residue gas exit conduit (14); the residue exit conduit (14) leading to a sixth-liquid separator with a gas exit conduit (15) and a liquid exit conduit (16); the gas exit conduit (15) leading to a seventh gas-liquid separator with a gas conduit (17) and a liquid exit conduit (18); the liquid exit conduits in the first, second, third, fourth, fifth, and sixth gas-liquid separators being joined into a conduit feeding to a eighth gas-liquid separator or stripper with gas and liquid exit ports.

\* \* \* \* \*

UNITED STATES PATENT AND TRADEMARK OFFICE
CERTIFICATE OF CORRECTION

PATENT NO. : 4,892,564
DATED : January 9, 1990
INVENTOR(S) : Thomas E. Cooley

It is certified that error appears in the above-identified patent and that said Letters Patent is hereby corrected as shown below:

In column 3, line 38; change "(Stream 7)" to --(Stream 5)--.

In column 4, line 17; change "Stream 25" to --Stream 26--.

In column 4, line 48; change "97841.270" to --9741.270--.

Signed and Sealed this

Fourteenth Day of May, 1991

*Attest:*

HARRY F. MANBECK, JR.

*Attesting Officer*  *Commissioner of Patents and Trademarks*